United States Patent [19]
Askin et al.

[11] Patent Number: 6,071,916
[45] Date of Patent: Jun. 6, 2000

[54] HIV PROTEASE INHIBITOR

[75] Inventors: David Askin, Warren; Robert M. Purick, Edison; R. Scott Hoerrner; Paul Reider, both of Westfield; Richard J. Varsolona, Scotch Plains; Ralph P. Volante, Cranbury, all of N.J.

[73] Assignee: Merck & Co., Inc., Rahway, N.J.

[21] Appl. No.: 09/086,021

[22] Filed: May 28, 1998

Related U.S. Application Data

[60] Provisional application No. 60/047,950, May 29, 1997.

[51] Int. Cl.$^7$ ................. A61K 31/495; C07D 405/06
[52] U.S. Cl. .............................. 514/253; 544/376
[58] Field of Search .................. 544/376; 514/253

[56] References Cited

U.S. PATENT DOCUMENTS

| | | | |
|---|---|---|---|
| 4,629,786 | 12/1986 | Debono et al. | 536/7.1 |
| 4,631,286 | 12/1986 | Shutske et al. | 514/297 |
| 5,646,148 | 7/1997 | Huff et al. | 514/253 |
| 5,717,097 | 2/1998 | Vacca et al. | 544/360 |

FOREIGN PATENT DOCUMENTS

95/16688   6/1995   WIPO .

*Primary Examiner*—Emily Bernhardt
*Attorney, Agent, or Firm*—Kenneth R. Walton; Melvin Winokur

[57]  ABSTRACT

This invention relates to a sulfate salt of an HIV protease inhibitor, Compound A, of formula:

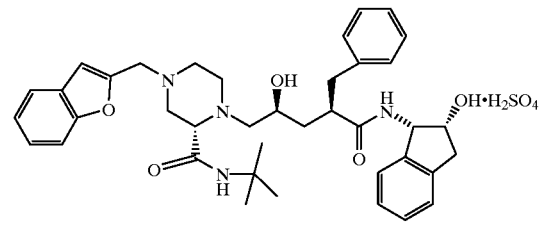

Compound A is useful in the treatment of AIDS, ARC or HIV infection in adults and children. Processes for making the sulfate salt of Compound A are also disclosed.

10 Claims, No Drawings

HIV PROTEASE INHIBITOR

This application claims the benefit of U.S. Provisional Application No. 60/047,950, filed May 29, 1997.

FIELD OF THE INVENTION

The present invention provides a pharmaceutically acceptable sulfate salt, and process for manufacture, of an HIV protease inhibitor. More specifically, the invention provides a sulfate salt of the HIV protease inhibitor, Compound A having substantially improved solubility in dilute HCl (gastric acid) solution which results in much greater oral absorption and bioavailability in animal models.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. Recently, a number of HIV protease inhibitor compounds have been disclosed as being useful in the treatment of infection by HIV and in the treatment of AIDS. These HIV protease inhibitor compounds and their utility in treating HIV and AIDS are described in PCT International Application Publication No. WO 95/16688, published Jun. 22, 1995. More particularly, the compound N-(2(R)-hydroxy-1(S)-indanyl)-2(R)-phenylmethyl-4-(S)-hydroxy-5-(1-(4-(2-benzo[b]furanylmethyl)-2(S)-N'-(t-butylcarboxamido)-piperazinyl))-pentaneamide, disclosed in Example 3 of WO 95/16688, and referred to herein as "Compound A," is a potent inhibitor of HIV protease and is useful in the treatment of infection by HIV and in the treatment of AIDS or ARC (AIDS related complex), without significant side effects or toxicity.

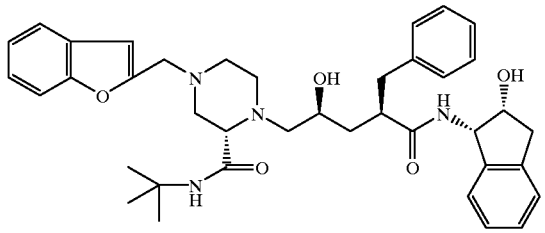

Compound A

Compound A is prepared according to the procedure of Example 3 in WO 95/16688 or according to the processes disclosed in detail herein. The identification of Compound A as an HIV protease inhibitor useful for treating AIDS was established according to the assays described in WO 95/16688.

Preparation of an acceptable salt of Compound A suitable for pharmaceutical development proved problematic. Numerous attempts to isolate a crystalline salt form of Compound A failed. Eventually, the problem of a pharmaceutically acceptable salt for the HIV protease inhibitor, Compound A, was solved by the synthesis of the HCl (dihydrate) salt. However, the HCl (dihydrate) salt had low solubility in dilute HCl (gastric acid) which resulted in poor oral absorption in animal models. Additionally, the HCl (dihydrate) had an extremely hydrophobic nature, requiring addition of wetting agents during formulation to achieve acceptable dispersion which increases the size of the solid dosage form or the number of pills required to achieve the desired dose, as well as the complexity and cost of the formulation, all of which are undesirable. These problems were solved by identification of the pharmaceutically superior sulfate salt of Compound A of the present invention. More specifically, the sulfate salt of the present invention has substantially improved solubility in dilute HCl (gastric acid) solution which results in much greater oral absorption and bioavailability in animal models. Additionally, the sulfate salt of Compound A is easy to formulate due to its hydrophilic nature, as compared to the HCl salt.

SUMMARY OF THE INVENTION

The present invention provides a compound of the formula

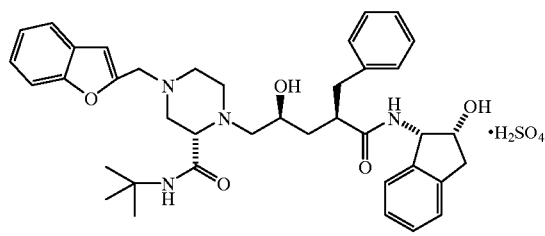

and solvates thereof.

In one embodiment of the invention is the compound

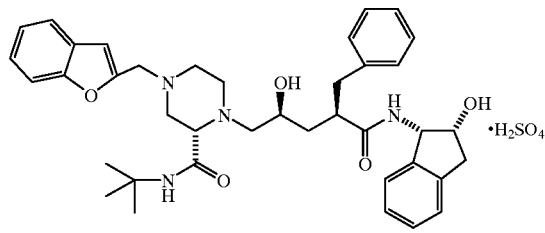

which is crystalline.

Preferably, the compound is the crystalline sulfate of Compound A

In a subclass of the invention is the compound characterized by differential scanning calorimetry (DSC) curve, at a heating rate of 10° C./min in an open cup under flowing nitrogen exhibiting an endotherm with an extrapolated onset temperature of about 190° C., a peak temperature of about 193° C. and an associated heat of about 120 J/gm.

Illustrative of the invention is the compound characterized by an x-ray powder diffraction pattern with d-spacings of 11.72, 5.56, 5.20, 5.00, 4.60, 4.50, 4.40, 4.26, 4.17, 4.08, 3.90, 3.81, 3.69, 3.24 and 3.33 Å.

An illustration of the invention is a pharmaceutical composition comprising any of the compounds described above and a pharmaceutically acceptable carrier.

Exemplifying the invention is a pharmaceutical composition made by combining any of the compounds described above and a pharmaceutically acceptable carrier.

An example of the invention is a process for making a pharmaceutical composition comprising combining any of the compounds described above and a pharmaceutically acceptable carrier.

Illustrating the invention are methods of inhibiting HIV protease, treating and/or preventing infection by HIV, and treating or preventing AIDS which comprises administering to a subject in need thereof a therapeutically effective amount of any of the compound or any of the compositions described above.

An additional illustration of the invention is the use of any of the compounds described above in the preparation of a medicament for: a) inhibiting HIV protease; b) treating or preventing infection by HIV protease; or c) treating or preventing AIDS; in a subject in need thereof.

Further exemplifying the invention is a process for making a compound of the formula

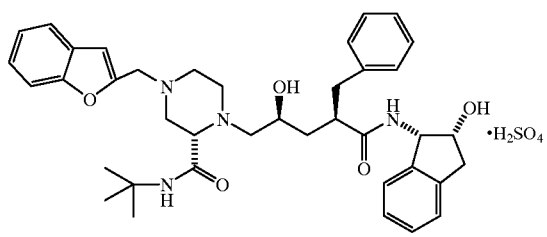

and solvates thereof, which comprises the steps of:
(a) dissolving the free base compound of the formula

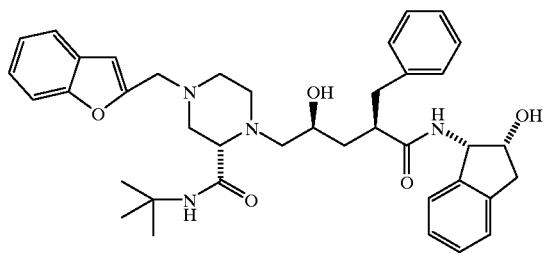

in a solvent to form a solution; and
(b) treating the solution from step (a) with sulfuric acid to form the compound

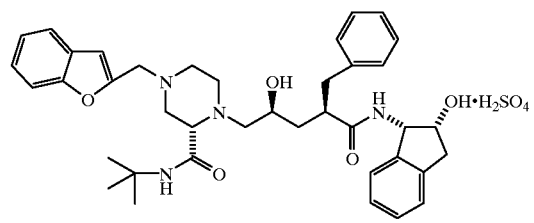

Further illustrating the invention is the process wherein the compound

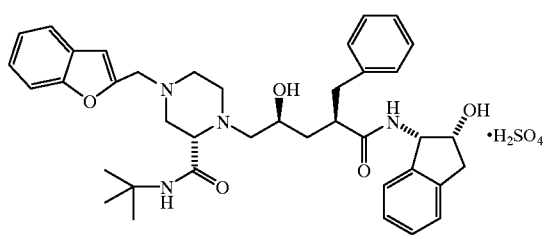

is crystalline.

Another example of the invention is the process wherein the solvent is selected from ethanol, ethyl acetate or isopropyl acetate.

More particularly illustrating the invention is a process for making a compound of the formula

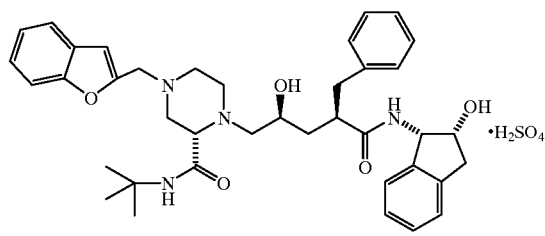

which comprises the steps of:
(a) dissolving the free base compound of the formula

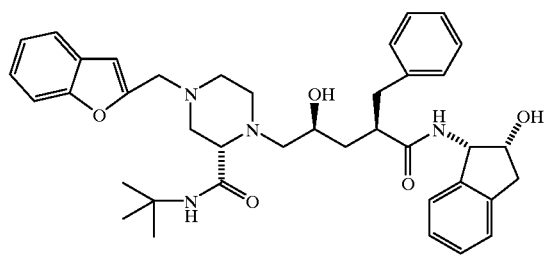

in ethanol to form a solution; and
(b) treating the solution from step (a) with a solution of sulfuric acid in ethanol to form the compound

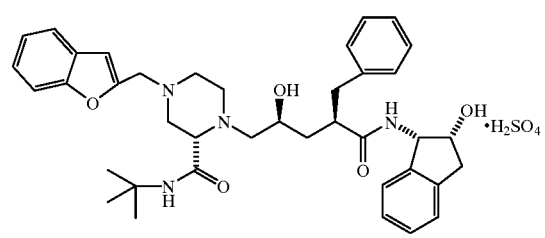

Preferably, the sulfate salt of Compound A is crystalline.

More specifically illustrating the invention is the process wherein the compound produced in step (b) is isolated at a temperature between about 15 and about 25° C.

More specifically exemplifying the invention is the process wherein the sulfuric acid in ethanol solution of step (b) is maintained at a temperature of below about +5° C. during the addition.

Another illustration of the invention is a compound made by
(a) dissolving a free base compound of the formula

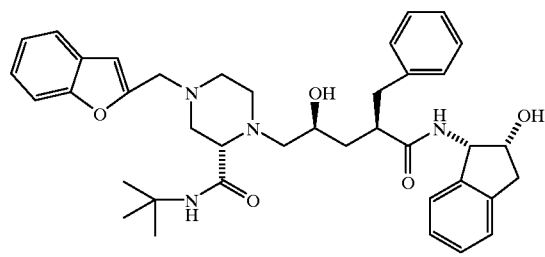

in ethanol to form a solution; and
(b) treating the solution from step (a) with a solution of sulfuric acid in ethanol to form the compound.

Preferably, the compound is isolated at a temperature between about 15 and about 25° C. and the sulfuric acid in ethanol solution of step (b) is maintained at a temperature of below about +5° C. during the addition.

DETAILED DESCRIPTION OF THE INVENTION

The present invention provides pharmaceutically superior salts of the potent HIV protease inhibitor, Compound A, pharmaceutical compositions containing them, and methods of making and using the pharmaceutically superior salts of Compound A. The Compound A sulfate salts and pharmaceutical compositions of the present invention are useful in the inhibition of HIV protease, the prevention and/or treatment of infection by human immunodeficiency virus (HIV) and the prevention and/or treatment of consequent pathological conditions such as AIDS, in adults, children or infants. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the salts and pharmaceutical compositions of this invention are useful in treating infection by HIV after suspected past exposure to HIV by, e.g., blood transfusion, exchange of body fluids, bites, accidental needle stick, or exposure to patient blood during surgery.

The term "Compound A," as used herein refers to the free base shown below:

Compound A

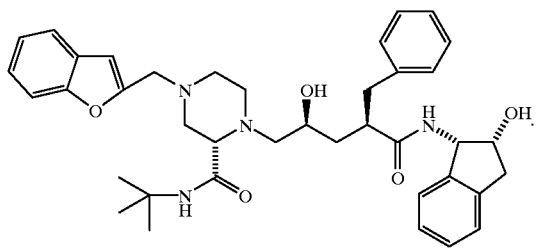

Compound A and its utility for inhibiting HIV protease and for treating and/or preventing AIDS is described in detail in WO 95/16688. Compound A is readily prepared according to the procedure of Example 3 in WO 95/16688, or according to the processes disclosed herein starting from the penultimate intermediate compound 6.

6

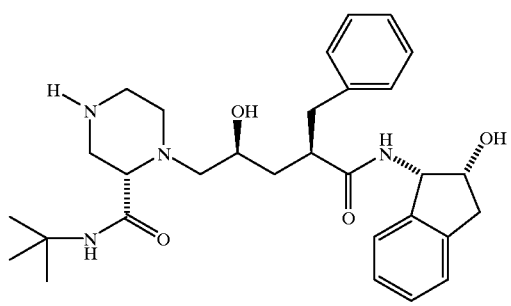

Compound 6 is prepared according to known procedures, for example, the processes disclosed in U.S. Pat. No. 5,618,937 (see, e.g., Examples 1–27 therein).

The invention involves the formation of a pharmaceutically superior sulfate salt of the HIV protease inhibitor, Compound A by treatment of the free base dissolved in a solvent with sulfuric acid. More specifically, the free base of Compound A is dissolved in a solvent and treated with about 1.0 to about 1.1 equivalents of sulfuric acid at a temperature of about 0 to about 40° C. to provide the sulfate salt of Compound A. If desired, the sulfuric acid can be added as a solution of sulfuric acid in the solvent. Preferably, about 1.0 equivalent of sulfuric acid is added to the solution of Compound A free base in the solvent at a temperature of about 10 to about 30° C., ideally the Compound A sulfate salt is isolated at a temperature between about 15 and about 25° C.

A wide variety of solvents can be utilized as long as the Compound A free base is soluble in the solvent. Thus, suitable solvents include, but are not limited to, water or esters, amides, ethers, alcohols and hydrocarbons containing water. Preferably, esters, alcohols or ethers containing water are used as the solvent; more preferably, alcohols or esters containing water; most preferably, ethanol, ethyl acetate or isopropyl acetate is utilized as the solvent. In a particularly preferred embodiment, ethanol is used as the solvent to provide the sulfate salt ethanolate of Compound A.

Thus, one aspect of the invention involves the formation of a pharmaceutically superior sulfate salt of the HIV protease inhibitor, Compound A by treatment of the free base in ethanol at a temperature between about 0 and about 25° C. (preferably, at about room temperature), with sulfic acid in ethanol solution kept at about −5° C. to about +5° C. followed by crystallization. The resulting sulfate salt is isolated as the crystalline sulfate salt of Compound A. It is advantageous to isolate the crystalline sulfate of Compound A at a temperature between about 15 and about 25° C. Other solvates of the sulfate are also accessible via this procedure by utilizing the solvents described previously in place of ethanol. The sulfate salt has desirable pharmaceutical properties, and is more rapidly absorbed than the existing HCl, HBr and methanesulfonate salts.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

As used herein, the term "composition" is intended to encompass a product comprising the specified ingredients in the specified amounts, as well as any product which results, directly or indirectly, from combination of the specified ingredients in the specified amounts.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

In general, the compounds of the present invention comprise Compound A as the sulfate salt. In a preferred embodiment, the compound comprises a crystalline sulfate salt of Compound A. In a particularly preferred embodiment, the compound comprises the crystalline sulfate salt ethanolate of Compound A; most preferably, the crystalline sulfate salt monoethanolate of Compound A.

The compounds of the present invention are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidity and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the instant specification, particularly the Schemes and Examples, are as follows:

Aq=aqueous

Ac=acetyl

EtOH=ethanol

IPAc=isopropyl acetate t-Bu=tertiary butyl

The following examples are provided to further define the invention without, however, limiting the invention to the particulars of these examples.

EXAMPLE 1

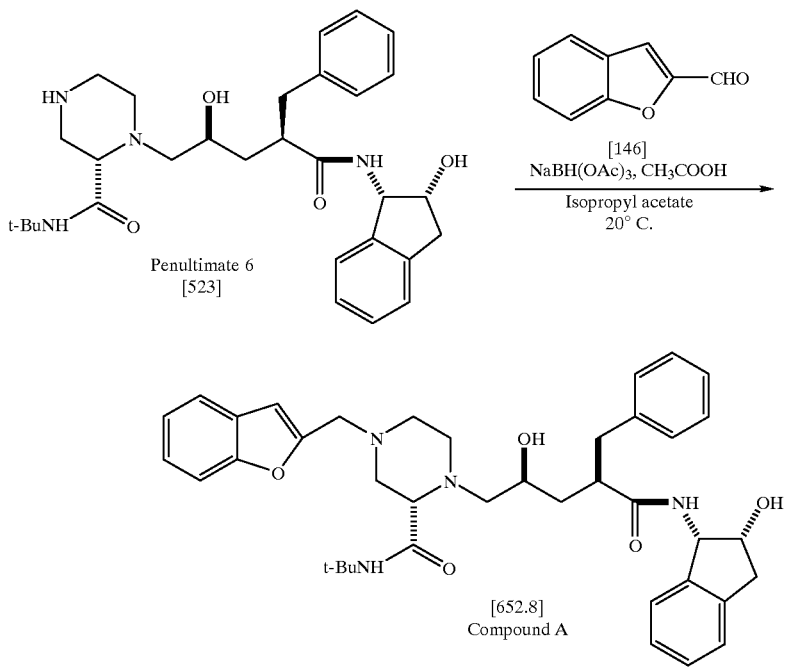

The IPAc/methanol solution (about 20% methanol in isopropyl acetate) containing the penultimate intermediate (70. 7 L, 8.66 mol, 4.53 kg) is concentrated in vacuo (25–46° C., 100 mm Hg) at about 20 L constant volume while adding fresh IPAc to perform a constant volume solvent switch to IPAc from the methanol/IPAc mixture. A final volume of 44 L and KF (Karl Fisher) titration for water of 994 mg/L is obtained. An NMR spectrum indicated no detectable methanol. Benzofuran 2-carboxaldehyde (1.49 kg, 9.70 mol) is added in one portion at 22–23° C. and 500 mL IPAc rinse was added. Sodium triacetoxyborohydride is charged as a solid over 10–15 min (2.90 kg, 13.0 mol) in one portion at ambient temperature and followed by a 500 mL IPAc flush. Glacial acetic acid is added (495 mL) at 27–28° C. and the mixture was aged for 2.5 h at 20–21° C. The reaction was quenched by the addition of 8 L of 13.8% aqueous $KHCO_3$ solution, evolution of gas (hydrogen) is observed. The combined batch is added to an extractor and additional aq $KHCO_3$ solution (16 L) and IPAc (15 L) is added. The mixture is agitated and the layers are separated and the IPAc phase is washed with additional aq $KHCO_3$ solution (24 L) then washed with 3×24 L deionized water. The washed crude Compound A free base solution is then combined with a similar solution resulting from parallel processing of an identically sized batch, and a constant volume distillation at 52 L was conducted at 15–18 in/Hg pressure with a batch temperature of 55–62° C. to a final KF of 330 mg/L. The resulting thick slurry was cooled from 60° C. to 3° C. over 4 h and the solids were isolated using a 23 inch filter pot; the cake was washed with cold 10° C. IPAc (10 L total) and the wet solid dried in a vacuum oven at 20° C.; 25–28 in/Hg with a nitrogen sweep to yield the Compound A freebase.

EXAMPLE 2

Benzofuran-2-carbinol Preparation

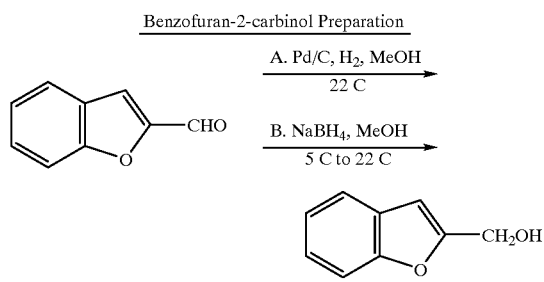

Method A:

Benzofiuran-2-carboxaldehyde (10.0 g, 68 mmol) was dissolved in methanol (90 mL). 5% Pd/C (0.500 g) was charged and the reaction mixture was hydrogenated for 4.5 hours at 40 psi $H_2$. The reaction was judged complete by tlc (4:1 hexanes/EtOAc) and the solution was filtered to remove the Pd/C and concentrated in vacuo to provide benzofuran-2-carbinol as an oil.

Method B:

Benzofuran-2-carboxaldehyde (10.0 g, 68 mmol) was dissolved in methanol (70 mL) and cooled to 5° C. Sodium borohydride (2.58 g, 68 mmol) was charged portionwise at 5° C. The batch was aged at 5° C. for 40 minutes and allowed to warm to room temperature (22° C.). The reaction was judged complete by tlc (4:1 hexanes/EtOAc) and the reaction mixture was cooled to 5° C. DI water (20 mL) was charged and the solution was concentrated in vacuo. EtOAc (80 mL) was charged and the solution was washed with DI water (2×20 mL). The EtOAc layer was concentrated in vacuo to provide benzofuran-2-carbinol as an oil.

EXAMPLE 3

Benzofuran-2-carbinol Preparation

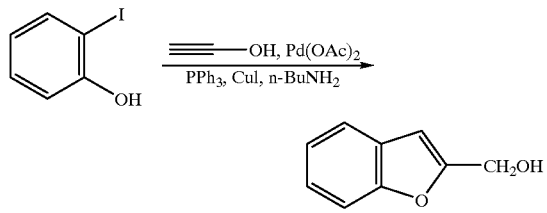

2-Iodophenol (500 mg, 2.27 mmol), propargyl alcohol (265 μl, 4.54 mmol), Pd(OAc)$_2$, (5.1 mg, 0.03 mmol), triphenylphosphine (12 mg, 0.046 mmol), n-butylamine (450 μL, 4.5 mmol) and CuI (8.6 mg, 0.045 mmol) were combined in 4.5 mL of THF and the mixture was heated at 40° C. under nitrogen for 36 h. The mixture was cooled to room temperature and the solvents were removed in vacuo and the residue purified by SiO$_2$ column chromatography on 100 g of silica gel, eluting with 20% ethyl acetate in hexanes. 2-(Hydroxymethyl)-benzofuran was obtained by concentration of the product containing fractions. [Kudu, N. G.; Pal, M.; Mahanty, J. S.; Dasgupta, F. K. *JCS Chem. Com.* 1992, 41]

EXAMPLE 4

Benzofuran-2-chloromethyl Preparation

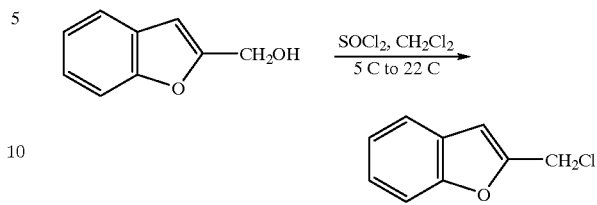

Method A:

Benzofuran-2-carbinol (10.38 g, 68.4 mmol) was dissolved in methylene chloride (100 mL) and cooled to 5° C. Thionyl chloride (5.49 mL, 75.2 mmol) was charged over 5 minutes and the reaction mixture was aged at 5° C. for 30 minutes and allowed to warm to 22° C. The reaction mixture was aged at 22° C. for 4 hours. The methylene chloride batch was washed with DI water (4×60 mL) and filtered through silica gel. The solution was concentrated in vacuo to provide a solid upon cooling. The crude solid was dissolved in hexanes (120 mL) and treated with Darco G-60 (1.0 g). The slurry was filtered and the solution was concentrated in vacuo to provide the benzofuiran-2-chloromethyl compound as a solid.

EXAMPLE 5

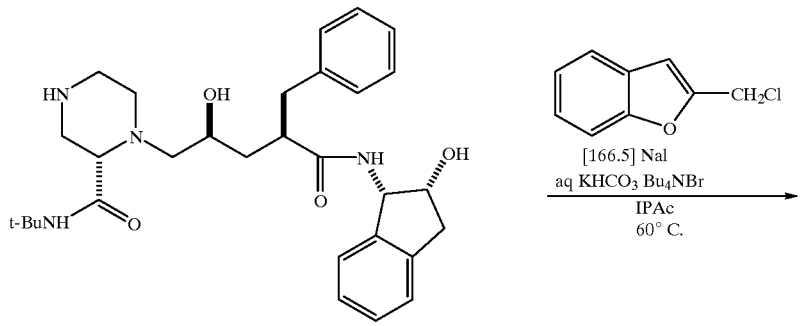

Penultimate 6
[523]

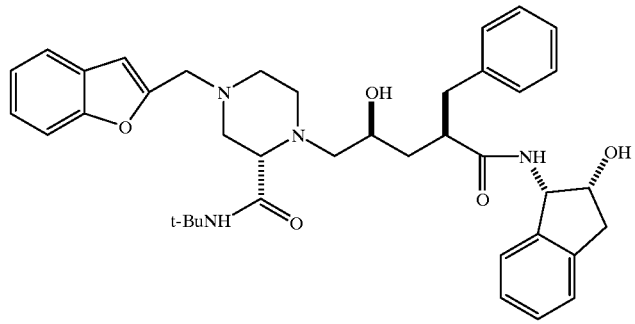

Compound A
[652.8]

The isolated penultimate solid (13.1 g, 25 mmol) was combined with IPAc (60 mL), water 20 mL), KHCO₃ (4.25 g, 42.5 mmol), sodium iodide (1.88 g, 12.5 mmol) and tetrabutylammonium bromide (600 mg, 1.86 mmol) and the mixture heated to 45° C. under nitrogen atmosphere. 2-(Chloromethyl)benzofuran (4.6 g, 27.5 mmol) was added and the resulting mixture was heated to 59–61° C. for 5 h. The mixture was allowed to cool to room temperature and diluted with IPAc (100 mL) and the aqueous layer was separated. The organic layer was washed with 3×50 mL water, then 50 mL brine solution and dried (MgSO₄) and the filtrate concentrated in vacuo and flushed with 100 mL IPAc and concentrated atmospherically to 80 mL, cooled to 25° C., seeded and aged with agitation for 2 h. The solids were filtered and washed with cold IPAc (2×15 mL) to afford Compound A free base.

EXAMPLE 6

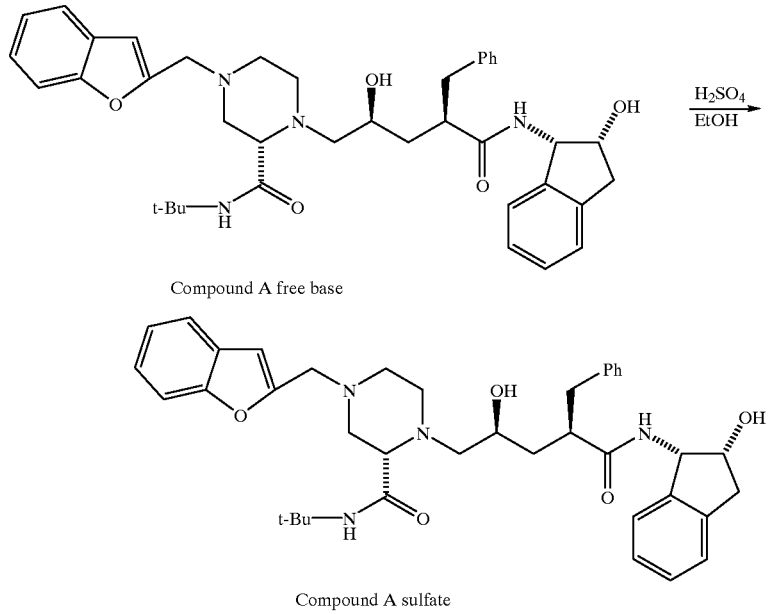

Compound A free base

Compound A sulfate

The Compound A freebase (25 g, 38.3 mmol) was dissolved in absolute ethanol (150 mL) at 22° C. The batch was filtered through a 5 μm filter and the filter flushed with absolute ethanol (50 mL). A solution of sulfuric acid/ethanol was prepared at <5° C. by charging concentrated sulfiric acid (3.91 g, 38.3 mmol) into a cooled solution (<5° C.) of absolute ethanol (50 mL) at such a rate that the temperature remained <5° C. A portion of the acid solution (10 mL, 20 vol %) was charged into the Compound A batch solution at 22° C. The Compound A batch may or may not be seeded at this point with Compound A•sulfate (500 mg) at 22° C. Ideally, the Compound A batch was seeded, as seeding relieves supersaturation during crystallization. The slurry was aged at 20–25° C. for 30 minutes. The remainder of the acid solution was charged into the batch via canula over 60 minutes. The batch temperature remained 20–25° C. during the addition (note: the acid solution was held at <5° C.) The final batch slurry was aged at 20–25° C. for 60 minutes and filtered. The cake was washed with absolute ethanol (2×25 mL) and dried in vacuo (25" Hg, 20° C.) for 18 hours with a nitrogen bleed to afford the Compound A sulfate. The sulfate is characterized by differential scanning calorimetry (DSC) curve, at a heating rate of 10° C./min in an open cup under flowing nitrogen exhibiting an endotherm with an extrapolated onset temperature of about 190° C., a peak temperature of about 193° C. and an associated heat of about 120 J/gm. Based on results of TG and TG-FTIR, the endotherm is due to the combination of the loss of the ethanol and melting with decomposition. The x-ray powder diffraction pattern is characterized by d-spacings of 11.72, 5.56, 5.20, 5.00, 4.60, 4.50, 4.40, 4.26, 4.17, 4.08, 3.90, 3.81, 3.69, 3.24 and 3.33 Å.

EXAMPLE 7

As a specific embodiment of an oral composition, 100 mg of the compound of Example 6 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A crystalline compound of the formula

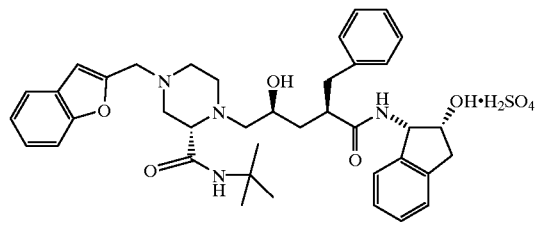

wherein the crystalline compound is characterized by (i) a differential scanning calorimetry (DSC) curve, at a heating rate of 10° C./min in an open cup under flowing nitrogen exhibiting an endotherm with an extrapolated onset temperature of about 190° C., a peak temperature of about 193° C. and an associated heat of about 120 J/gm and (ii) an X-ray powder diffraction pattern with d-spacings of 11.72, 5.56, 5.20, 5.00, 4.60, 4.50, 4.40, 4.26, 4.17, 4.08, 3.90, 3.81, 3.69, 3.24 and 3.33 Å.

2. A pharmaceutical composition comprising the compound of claim 1 and a pharmaceutically acceptable carrier.

3. A pharmaceutical composition made by combining a compound of claim 1 and a pharmaceutically acceptable carrier.

4. A process for making a pharmaceutical composition comprising combining a compound of claim 1 and a pharmaceutically acceptable carrier.

5. A method of treating infection by HIV which comprises administering to a subject in need thereof a therapeutically effective amount of the compound of claim 1.

6. A method of treating AIDS which comprises administering to a subject in need thereof a therapeutically effective amount of the compound of claim 1.

7. A method of inhibiting HIV protease which comprises administering to a subject in need thereof a therapeutically effective amount of the compound of claim 1.

8. A method of treating infection by HIV which comprises administering to a subject in need thereof a therapeutically effective amount of the composition of claim 2.

9. A method of treating AIDS which comprises administering to a subject in need thereof a therapeutically effective amount of the composition of claim 7.

10. A method of inhibiting HIV protease which comprises administering to a subject in need thereof a therapeutically effective amount of the composition of claim 2.

* * * * *